(12) United States Patent
Ho

(10) Patent No.: US 8,028,692 B2
(45) Date of Patent: Oct. 4, 2011

(54) MULTI-SECTIONED CONDUIT ASSEMBLY

(75) Inventor: Peter Chi Fai Ho, Pittsburgh, PA (US)

(73) Assignee: RIC Investments, LLC, Wilmingtomn, DE (US)

( * ) Notice: Subject to any disclaimer, the term of this patent is extended or adjusted under 35 U.S.C. 154(b) by 747 days.

(21) Appl. No.: 11/715,622

(22) Filed: Mar. 8, 2007

(65) Prior Publication Data

US 2007/0215147 A1    Sep. 20, 2007

Related U.S. Application Data

(60) Provisional application No. 60/780,587, filed on Mar. 9, 2006.

(51) Int. Cl.
*A62B 7/12* (2006.01)

(52) U.S. Cl. .......... 128/200.24; 128/202.27; 128/204.18

(58) Field of Classification Search ............ 128/200.24, 128/201.13, 202.27, 203.12, 203.15–203.17, 128/203.26, 203.27, 204.17, 204.18, 204.21, 128/206.21, 912; 604/523–539, 284; 285/272, 285/147.1, 305, 921

See application file for complete search history.

(56) References Cited

U.S. PATENT DOCUMENTS

| 1,248,558 | A | * | 12/1917 | Scribner | 285/70 |
|---|---|---|---|---|---|
| 1,673,338 | A | * | 6/1928 | Mitchell | 285/86 |
| 1,737,465 | A | * | 11/1929 | Lindsey | 285/13 |
| 2,476,398 | A | * | 7/1949 | Baumann | 439/17 |
| 2,695,794 | A | * | 11/1954 | Davis et al. | 285/31 |
| 3,243,206 | A | * | 3/1966 | Samer | 285/154.1 |
| 3,339,946 | A | * | 9/1967 | Kreidel, Sr. et al. | 285/272 |
| 3,556,097 | A | | 1/1971 | Wallace | |
| 4,948,925 | A | * | 8/1990 | Winters et al. | 175/48 |
| 4,967,744 | A | | 11/1990 | Chua | |
| 5,507,535 | A | * | 4/1996 | McKamey et al. | 285/149.1 |
| 5,572,994 | A | | 11/1996 | Smith | |
| 5,673,687 | A | | 10/1997 | Dobson et al. | |
| 5,775,741 | A | * | 7/1998 | Rice et al. | 285/272 |
| 5,816,624 | A | * | 10/1998 | Smith | 285/276 |
| 6,733,046 | B1 | * | 5/2004 | Rief | 285/276 |
| 7,174,893 | B2 | * | 2/2007 | Walker et al. | 128/206.21 |
| 7,278,423 | B2 | * | 10/2007 | Serowski et al. | 128/202.27 |
| 2002/0070550 | A1 | * | 6/2002 | Lin et al. | 285/305 |

OTHER PUBLICATIONS

PCT Search Report and Written Opinion, Dec. 12, 2007.

* cited by examiner

*Primary Examiner* — Justine Yu
*Assistant Examiner* — Latoya M Louis
(74) *Attorney, Agent, or Firm* — Michael W. Haas

(57) ABSTRACT

A conduit assembly that delivers a flow of breathing gas to an airway of user. The conduit assembly includes a first flexible segment having a first end portion, a second end portion, and a first lumen defined therein from the first end portion to the second end portion. The conduit assembly also includes a second flexible segment having a third end portion, a fourth end portion, and a second lumen defined therein from the third end portion to the fourth end portion. A first swivel connector is coupled to the second end portion of the first segment and the third end portion of the second segment such that the first segment is rotatable relative the second segment.

19 Claims, 6 Drawing Sheets

MULTI-SECTIONED CONDUIT ASSEMBLY

CROSS-REFERENCE TO RELATED APPLICATIONS

This application claims priority under 35 U.S.C. §119(e) from provisional U.S. patent application No. 60/780,587 filed Mar. 9, 2006, the contents of which are incorporated herein by reference.

BACKGROUND OF THE INVENTION

1. Field of the Invention

The present invention relates to a conduit assembly for use in a gas flow delivery system, and, in particular, to a conduit assembly that includes a plurality of flexible segments rotatably coupled to one another to prevent torque from being transferred along the conduit assembly.

2. Description of the Related Art

Gas flow delivery systems are used to deliver a flow of gas to an airway of a subject. Such systems are typically used in the medical field to deliver gas to a patient. Examples of gas flow delivery systems in the medical field include a ventilator or respirator, which replaces or supplements a patient's respiration, and a pressure support system, which provides a flow of gas to an airway of a patient at an elevated pressure to treat a medical disorder, such as obstructive sleep apnea (OSA). Pressure support systems include, but are not limited to continuous positive airway pressure (CPAP) devices, which deliver a constant positive pressure to the airway of a patient over multiple respiratory cycles, and variable pressure devices, where the pressure of the flow of gas delivered to the patient is variable.

Variable pressure support devices include auto-titrating devices that are capable of changing a base pressure or pressure profile delivered to the patent based on a monitored condition of the patient. Other variable pressure devices change the pressure of the flow of gas during a respiratory cycle. These devices include the following: a proportional assist ventilation (PAV®), a proportional positive airway pressure (PPAP®) device, a C-Flex™ device, a Bi-Flex™ device, and a BiPAP® device manufactured and distributed by Respironics, Inc. of Pittsburgh, Pa. The BiPAP device is a bi-level pressure support system in which the pressure provided to the patient varies with the patient's respiratory cycle so that a higher pressure is delivered during inspiration than during expiration.

A typical gas flow delivery system comprises a pressure/flow generating system that produces a flow of gas for delivery to a patient and a system for communicating the flow of gas to the patient. The latter system typically includes a flexible conduit having one end coupled to the pressure/flow generating device and a second end portion that couples to an airway of patient by means of a patient interface assembly worn by the patient. The conduit, which is also referred to as an air hose or patient circuit, carries the flow of gas from the pressure generating device during operation of the system. The patient interface assembly, typically in the form of a nasal, oral, or nasal/oral mask, attached to the user via a headgear is coupled to the second end portion of the conduit to communicate the flow of gas from the patient circuit to the airway of the patient.

Conventional patient circuits are typically six feet long and have a smooth internal surface to minimize the resistance the flow of gas through the tube. A continuous helix is typically provided in the exterior of the time to protect it from collapsing. While this helix serves to provide structural support for the hose, it also induces a problem with respect to the management of the hose. In particular, the increased structural support causes any loading and twisting at one portion of the hose to be carried or transferred along the entire length of the hose. This is particularly problematic because, as noted above, one end of the patient circuit is coupled to patient interface being worn by the user. Thus, torque or twisting at one location on the conventional patient circuit is readily transferred to the patient interface.

Conventional patient interfaces are typically unable to tolerate torque being applied to them by the patient circuit. This torque can cause the patient interface to be dislodged from the user or compromise the seal between the patient interface and the surface of the user, i.e., create a leak in the gas flow system at the surface of the user. Torque on the patient interface can also cause the mask to be uncomfortable to the user by applying more force that desired to a given part of the user's face.

SUMMARY OF THE INVENTION

Accordingly, it is an object of the present invention to provide a patient circuit that overcomes the shortcomings of conventional patient circuit. This object is achieved according to one embodiment of the present invention by providing a patient circuit that includes a first flexible segment having a first end portion, a second end portion, and a first lumen defined therein from the first end portion to the second end portion. In addition, the patient circuit includes a second flexible segment having a third end portion, a fourth end portion, and a second lumen defined therein from the third end portion to the fourth end portion. Finally, a first swivel connector is coupled to the second end portion of the first segment and the third end portion of the second segment such that the first segment is rotatable relative the second segment. This rotatable connection prevents torque generated at one location on the patient circuit from being transferred to another location.

In is yet another object of the present invention to provided a system for delivering a breathing gas to a user that includes such a patient circuit. In an exemplary embodiment of the present invention, such a system includes a gas flow generating device adapted to produce a flow of gas, a patient interface assembly, and a conduit assembly. The gas flow generating device has a housing and an gas flow outlet is provided on an exterior of the housing. A first end portion of the conduit assembly is operatively coupled to the outlet of housing, and a second end portion of the conduit assembly is operatively coupled to the patient interface assembly. The conduit assembly carries the flow of gas from the gas flow generating device during operation of the gas flow generating system. The conduit assembly comprises a plurality of flexible segments, and a swivel connector disposed between and joining adjacent segments in the plurality of flexible segments such that adjacent flexible segments are rotatable relative to one another. As noted above, this swivel coupling prevents torque from being transferred along the conduit assembly, and, in particular, to the patient interface assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration

DETAILED DESCRIPTION OF THE EXEMPLARY EMBODIMENTS

Figure 1:
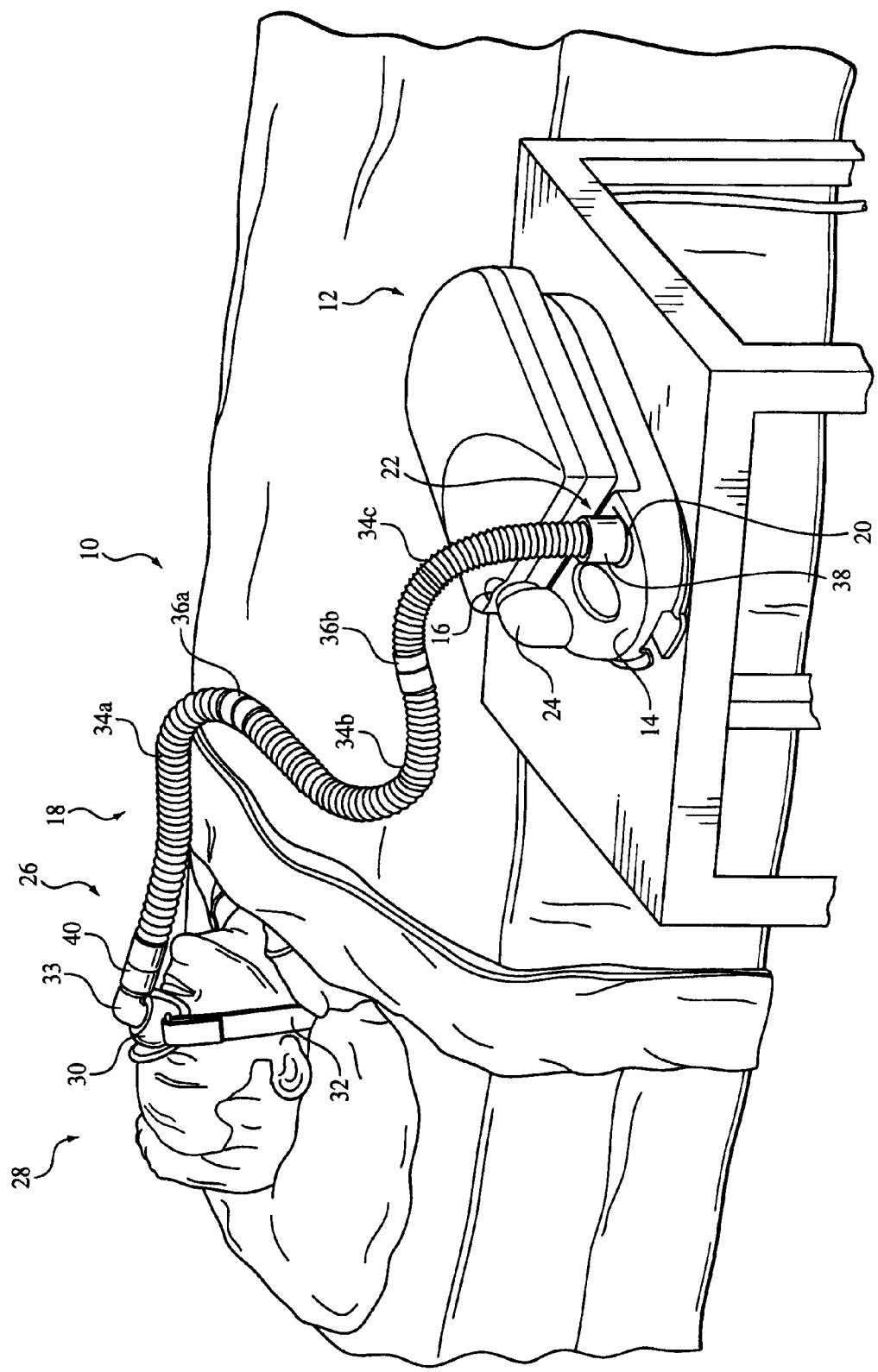
FIG. 1 is a perspective view of a pressure support system that includes a first embodiment of a conduit assembly according to the principles of the present invention.
Figure 2:
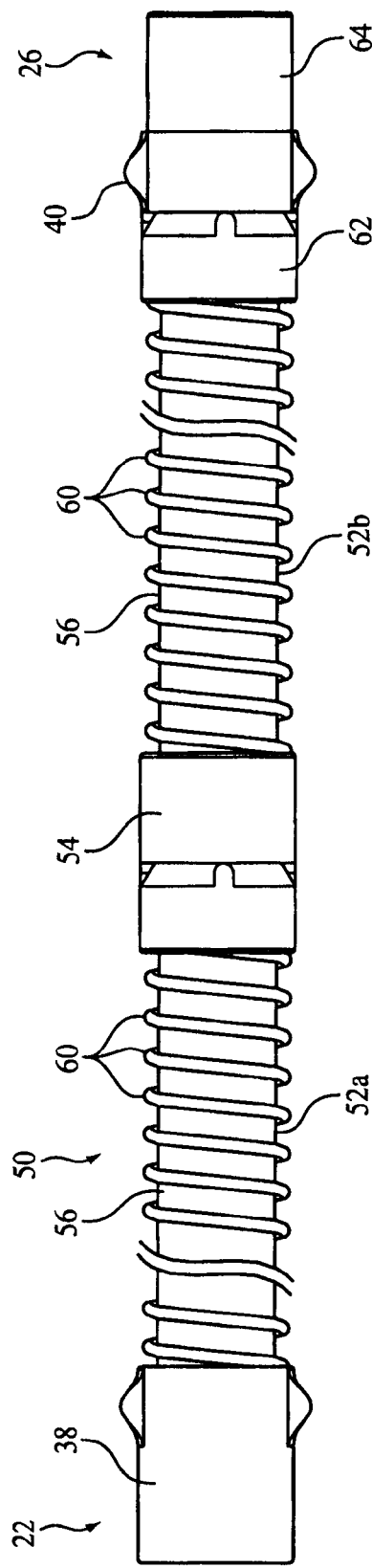
FIG. 2 is a side view illustrating two sections in the conduit assembly according to the principles of the present invention.
Figure 3:
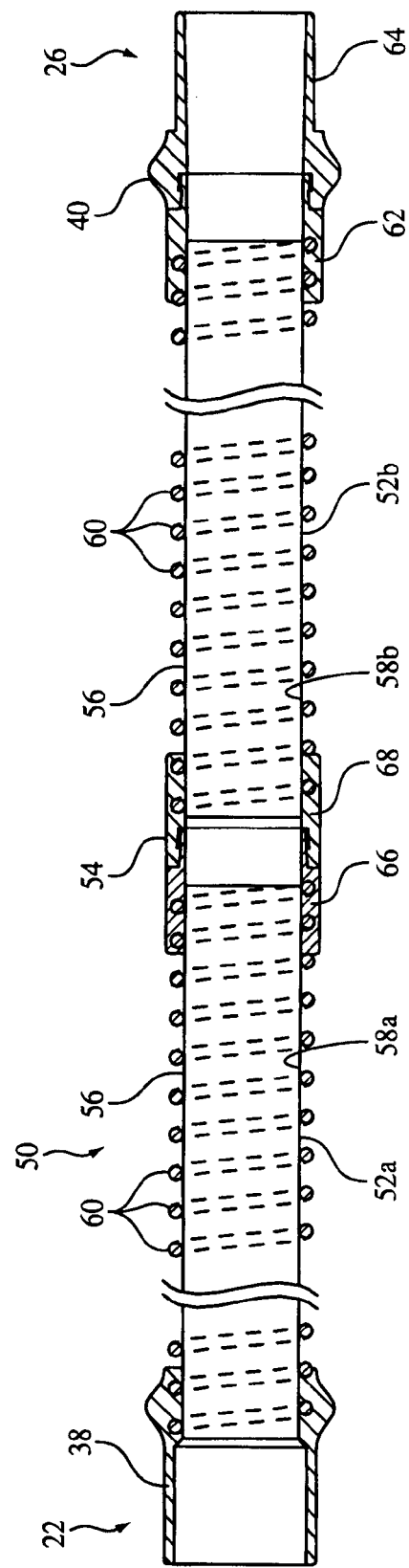
FIG. 3 is a cross-sectional view of the conduit assembly of FIG. 2.

Referring now to FIG. 1, a gas flow delivery system 10 for delivering a flow of gas to an airway of a patient is illustrated. Gas flow delivery system 10 comprises a pressure and/or flow generating device 12 that produces a flow of gas and an optional humidifier 14 coupled to an outlet 16 of pressure/flow generating device 12. A conduit assembly 18 according to the principles of the present invention is coupled to an outlet 20 of the humidifier. Of course, if the humidifier is omitted, conduit assembly 18 would be coupled to outlet 16 of pressure/flow generating device 12.

Pressure/flow generating device 12 is any conventional ventilator, pressure support system, or other device that is used to communicate a flow of gas or gas at an elevated pressure above the ambient pressure to the airway of the user. Examples of such systems include, but are not limited to: a ventilator, continuous positive airway pressure (CPAP) device, or a variable pressure device, e.g. an auto-titrating device, proportional assist ventilation (PAV®) device, proportional positive airway pressure (PPAP®) device, C-Flex™ device, Bi-Flex™ device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device. Other devices that communicate a flow of gas with an airway of a patient suitable for use in with the present invention include devices that apply a high and low or positive and negative pressure to the airway for purposes of secretion clearance or loosening.

Conduit assembly 18 has a first end portion 22 operatively coupled to an outlet 24 of humidifier 14 (or to an outlet 16 of pressure support system 12 if the humidifier is omitted) and a second end portion 26. A lumen is defined through the patient circuit from the first end portion to the second end portion so that a flow of gas is carried from the humidifier or the pressure generating device to the patient during operation of the gas flow generating system.

A patient interface assembly 28, which typically includes a mask 30, a headgear 32, and a conduit coupling 33, is coupled to second end portion 26 of conduit assembly 18. More specifically, conduit coupling 33 in the patient interface assembly is coupled to second end portion 26. In the illustrated exemplary embodiment of the present invention, patient interface assembly 28 is a nasal mask that seals around the patient's nares. It is to be understood, however, that patient interface assembly 28, can include a nasal mask, nasal pillows, nasal/oral mask, full face or total mask, hood, tracheal tube, endotracheal tube, or any other device that communicates a flow of gas from the patient circuit to the airway of the patient. Conduit coupling 33 is typically an elbow that is rotatably coupled to the shell of the mask. However, the present invention contemplates that the conduit coupling can have any other configuration or can be omitted entirely.

It is to be further understood that various components may be provided in or coupled to the conduit assembly 18. For example, a bacteria filter, pressure control valve, flow control valve, pressure/flow/temperature/humidity sensor(s), meter, pressure filter, humidifier, and/or heater can be provided in or attached to the conduit assembly.

Gas flow delivery system 10 shown in FIG. 1 is a single-limb system, meaning that the conduit assembly 18 includes only one gas delivery conduit connecting the patient to the pressure generating device. In a single-limb system, an exhaust assembly (not shown) is provided in the patient conduit for venting gases, such as the patient's exhaled gases, from the system. The exhaust assembly can be provided on the patient interface assembly and/or on the patient circuit and can have a wide variety of configurations depending on the desired manner in which gas is to be vented from the pressure support system.

The present invention also contemplates that the gas flow generating system can be a two-limb system, which includes a delivery conduit and an exhaust conduit operatively connected to the airway of the patient. A key difference between a single-limb system and a two-limb system is that in a two-limb system, there is an exhaust conduit that carries exhaust gas from the patient. An exhaust valve is also typically provided at the end of the exhaust conduit distal from the patient. The exhaust valve is normally actively controlled to maintain a desired level of pressure in the system, which is commonly known as positive end expiratory pressure (PEEP). This is accomplished by controlling the flow of exhaust gas from the otherwise closed system.

Conduit assembly 18 includes plurality of flexible segments 34a, 34b, and 34c. In the embodiment illustrated in FIG. 1, conduit assembly 18 includes three such segments. Each segment is coupled to an adjacent segment via a swivel connector 36a and 36b. An outlet connector 38 is provided at first end portion 22 of conduit assembly 18, and a patient interface connector 40 is provided at second end portion 26. Details of each of these features are discussed below.

In an exemplary embodiment of the present invention, patient interface connector 40 is a swivel connector so that the flexible segment adjacent to the patient interface is rotatable relative to the conduit coupling 33. In addition, outlet connector 38 is a rubber cuff that attaches to the outlet of the pressure support system in a fixed position. It is to be understood that connector 40 can be replaced by connector 38 and vice versa. The present invention further contemplates attaching the patient interface device, such as the shell of the mask, to the flexible segment directly, eliminating conduit coupling 33 and patient interface connector 40.

By allowing each flexible segment to rotate relative to the adjacent flexible segment using the swivel connector, torque applied to one portion of the conduit assembly is prevented or from being transferred to another location, namely the patient interface assembly provided as the end of the conduit assembly. That is, the torque produced at one location on the conduit assembly will result in rotation of the flexible segment and will not be imparted to the patient interface, where it may act to dislodge or dislocate the interface on the user. Even if not completely prevented, the swivel connector will minimize the amount of torque that is transfer along the length of the conduit assembly.

It should be further understood that patient interface assembly 28 is subjected to two types of torque. First, the torque exerted on the interface by the weight of conduit through the series of connectors, which act as the moment arm. Whatever portion of the conduit that hangs or suspense over any non-supported area will contribute to this torque. Second, is the torque exerted on the patient interface by the twisting or screwing motion around the axis of the conduit when the end user moves. It is this second torque that the multi-segment conduit assembly attempts to minimize.

The present invention contemplates that the conduit assembly can include as few as two flexible segments and can include more than three such segments. That is, any number of flexible segment can be used to form the conduit assembly. It is typical in the medical industry that patient circuits have a predetermined length that is standard for the industry. This length, as well as the configuration of the conduit assembly, determines the pressure drop along the length of the conduit assembly. For many pressure support devices, this pressure drop must be within a certain range in order to the pressure support system to deliver the appropriate pressure level. Thus, industry standard lengths and bore sizes have been adopted. For this reason, the present invention contemplate that the segments, when assembled, form a conduit assembly that comports to the standards in the industry, i.e., has a certain length.

Although a generally tubular configuration has been illustrated for conduit assembly 18 and the segments thereof, the present invention contemplates that the conduit assembly, or segments thereof, can have any other shape, i.e., non-cylindrical, so long at it accomplishes the function of carrying a flow of fluid from one place to another. In addition, each segment can have a different length, diameter, or configuration from the other segments forming the conduit assembly. It should also be understood that other configurations for the coupling members provided at the ends of the conduit assembly are contemplated by the present invention.

The details of a conduit assembly 50 that includes only two flexible segments is shown in FIGS. 2-5. Conduit assembly 50 is similar to conduit assembly 18 of FIG. 1 except that it includes fewer flexible segments and swivel connectors. The structural features of the flexible segments, swivel connector, outlet connector 38 provided at first end portion 22 of the conduit, and patient interface connector 40 provided at second end portion 26 are the same as that used in the conduit assembly of FIG. 1.

Conduit assembly 50 includes a first flexible segment 52a and a second flexible segment 52b coupled to one another via a swivel connector 54. Outlet connector 38 is provided at first end portion 22 of conduit assembly 50, which is the end that attached to the pressure/flow generating system. Patient interface connector 40 is provided at second end portion 26 of the conduit assembly that corresponds to the end that attaches to the patient interface assembly.

Each flexible segment includes a relatively flexible member 56 formed from a material, such as EVA, Polypropylene, Polyethylene, or Polyester Elastomer. This flexible member forms a tube or conduit having a lumen 58a, 58b defined therein that serves as the gas flow passage through the conduit assembly. Depending on the material selected and/or its dimensions, the flexible member alone forms the flexible segment. However, the present invention contemplates providing a helical support 60 around the flexible member so that the flexible member can be made relatively lightweight while still providing a conduit assembly that is structurally sound.

In an exemplary embodiment, helical support 60 is formed from a flexible material that is more rigid than that of flexible member 56. Example of such material include EVA, Polypropylene, Polyethylene, High Density Polyethylene, Polyethylene, or Polyester Elastomer. It is to be understood that the helical support can be made from any suitable material or combination of materials. For example, the present invention contemplate using a helical material that includes a wire or plurality of wires embedded in the material forming the helical support. Such wires can be used for heating the conduit assembly or carrying signals. The shape, materials, number of turns per unit of length, location of the embedded materials in the helical support, dimensions, or any other feature of the helical support can be altered while still keeping within the principles of the present invention.

In an exemplary embodiment of the present invention, outlet connector 38 is formed either from a flexible material, such as rubber or silicone, so that it is capable of being friction fit to a male outlet portion of the pressure/flow generating system, or from a relatively rigid material, such as PP, HDPE or Polycarbonate, in the dimensions of standard fitting, often conical taper fit to a male outlet portion of the pressure/flow generating system. The outlet connector is bonded to the end portion of the flexible member in the associated flexible segment. In an exemplary embodiment, outlet connector is joined to flexible member by an adhesive or a weld, such as a hot weld or over-molding. The outlet connector also includes grooves to receive the helical supports. It is to be understood that the outlet connector can be made from any suitable material or combination of materials, including rigid, non-rigid, or semi-rigid materials. In addition, the outlet connector can have any shape, size, or configuration so long as it is suitable for its intended purposes.

Patient interface connector 40 includes a first portion 62 bonded to the end portion of the flexible member in the associated flexible segment and a second portion 64 rotatably coupled to the first portion. That is, first portion 62 is coaxial with second portion 64 so that one portion can rotate around this central axis with respect to the other portion. First portion 62 of patient interface connector 40 is bonded to the flexible member using any conventional technique, such as an adhesive or a weld, such as a hot weld or over-molding. In addition, the present invention contemplates providing grooves 65 in the first portion to receive the helical supports. First portion 62 is coupled to second portion 64 in any conventional manner. For example, a tongue 61 and groove 63 configuration can be used to couple these two elements.

Patient interface connector 40 or the components thereof can have any shape, size, or configuration so long as it is suitable for its intended purposes. The patient interface connector and/or the components thereof can be made from any suitable material or combination of materials, including rigid, non-rigid, or semi-rigid materials. The present invention also contemplates that the patient interface connector can be formed from a single component, or from multiple components, which need rotate relative to one another. Patient interface connector 40 can also be configured as described above with respect to outlet connector 38. Conversely, outlet connector 38 can also be configured as described above with respect to patient interface connector 40.

Figure 4:
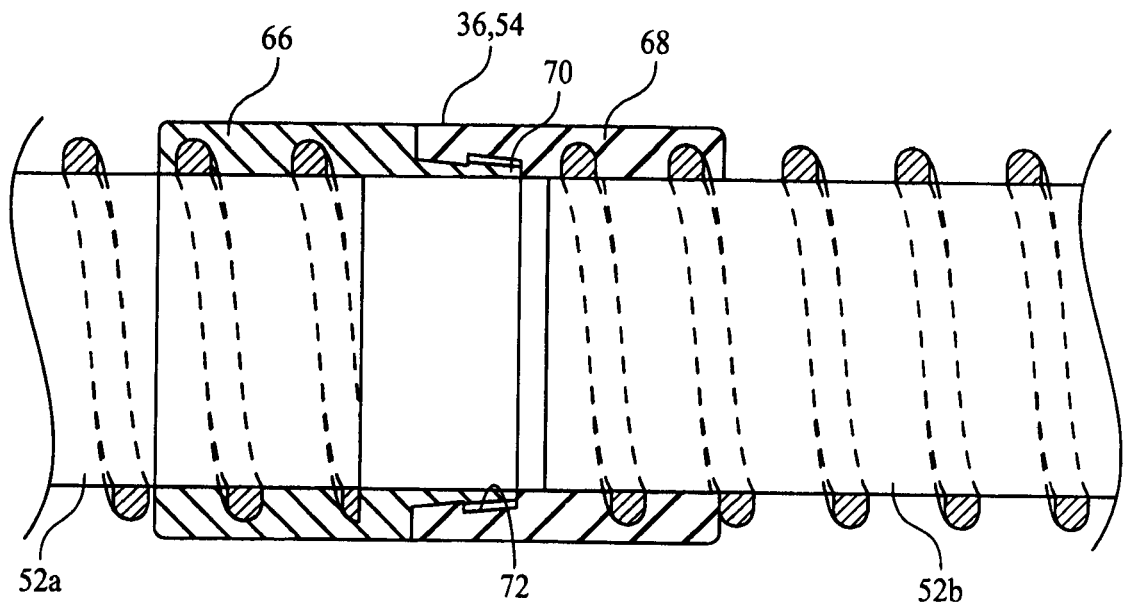
FIG. 4 is a cross-sectional view of the swivel connector used in the conduit assembly of FIG. 1.
Figure 5:
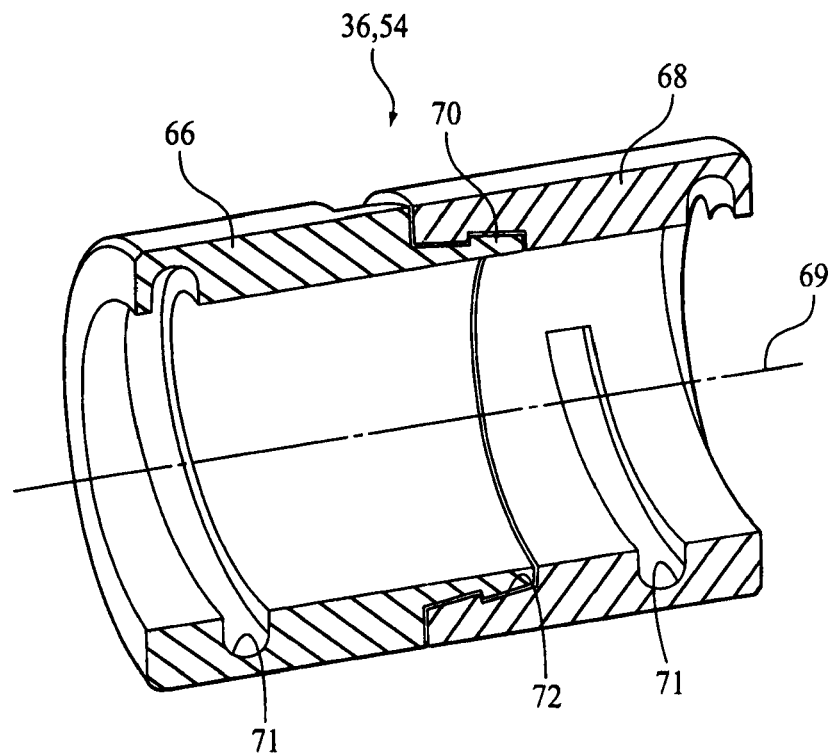
FIG. 5 is a cross-sectional perspective view of the swivel connector used in the conduit assembly of FIG. 1.
Figure 6A:
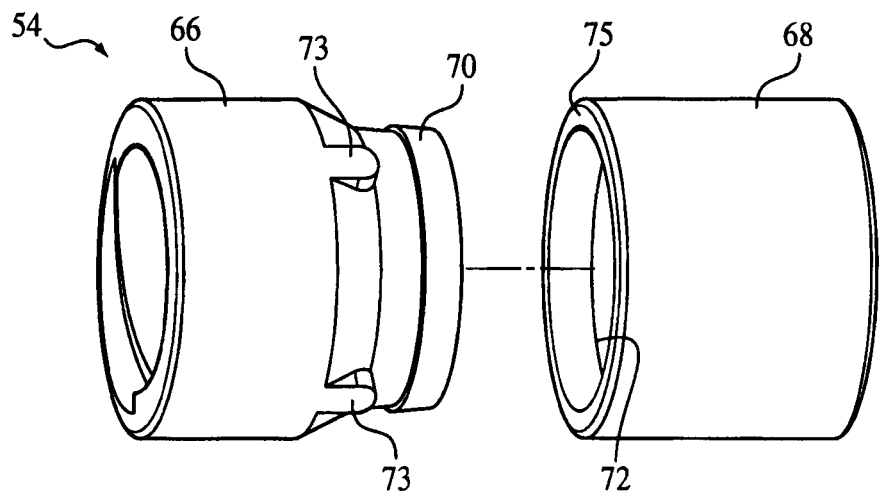
FIGS. 6A and 6B are perspective views illustrating the portions of the swivel connector used on the conduit assembly of FIG. 1 shown in the uncoupled and coupled positions, respectively.
Figure 6B:
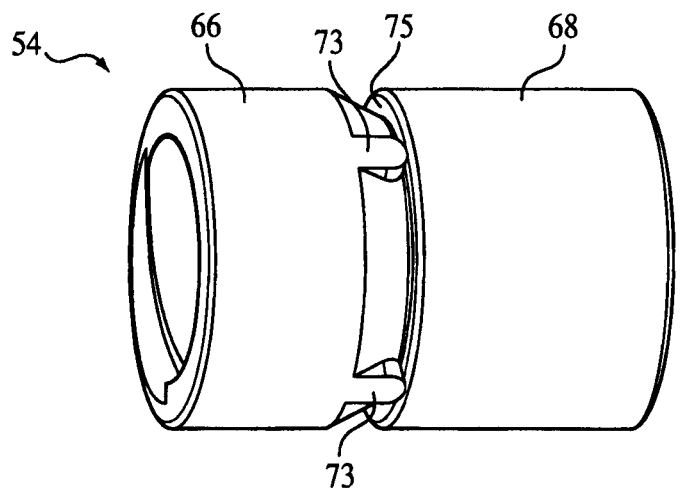
Figure 7:
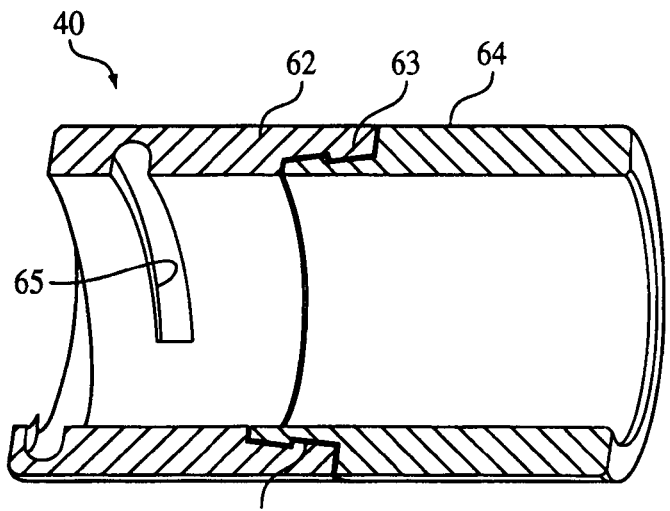
FIG. 7 is a cross-sectional perspective view of the patient interface connector used on the conduit assembly of FIG. 1.

As noted above, swivel connector 54 is connected to one end of first flexible segment 52a and to an adjacent end of flexible segment 52b. FIGS. 4 and 5 are cross-sectional views illustrating the details of the swivel connector. In the illustrated exemplary embodiment, swivel connector 54 includes a first portion 66 bonded to the end portion of flexible segment 52a and a second portion 68 bonded to the end portion of flexible segment 52b. In addition, first portion 66 is rotatably coupled to second portion 68. More specifically, first portion 66 is coaxially aligned and coupled to with second portion 68 such that one portion can rotate around a central axis 69 with respect to the other portion. First portion 66 is coupled to the second portion 68 in any conventional manner so as to allow rotational movement between these two member. For example, a tongue 70 and groove 72 configuration can be used to couple these two elements. The tongue and groove can be engaged by means of a snap fit.

In the illustrated embodiment of FIG. 5, first portion 66 of swivel connector 54 includes a plurality of structures 73 provided on the periphery of the connector. Structures 73 engage the end surface 75 of second portion 68 to reduce or to minimize the friction between the two components by creating a point-contact instead of a complete face-to-face or line contact on the circumference which would be the case if structures 73 were not provided. In the illustrated embodiment, the structures 73 are integrally formed with and not movable relative to first portion 66 of swivel connector 54. In the illustrated embodiment, four structures 73 are provided on first portion 66. It is to be understood that more or less structures can be provided and that these structures can have other configurations.

First and second portions 66 and 68 of swivel connector 54 are bonded to the respective flexible members using any conventional technique, such as an adhesive or a weld, such as a hot weld or over-molding. In addition, the present invention contemplates providing grooves 71 in the first and/or second portions to receive the helical supports. Swivel connector 54 or the components thereof can have any shape, size, or configuration so long as it is suitable for its intended purposes. Swivel connector 54 and/or the components thereof can also be made from any suitable material or combination of materials, including rigid, non-rigid, or semi-rigid materials.

Figure 8:
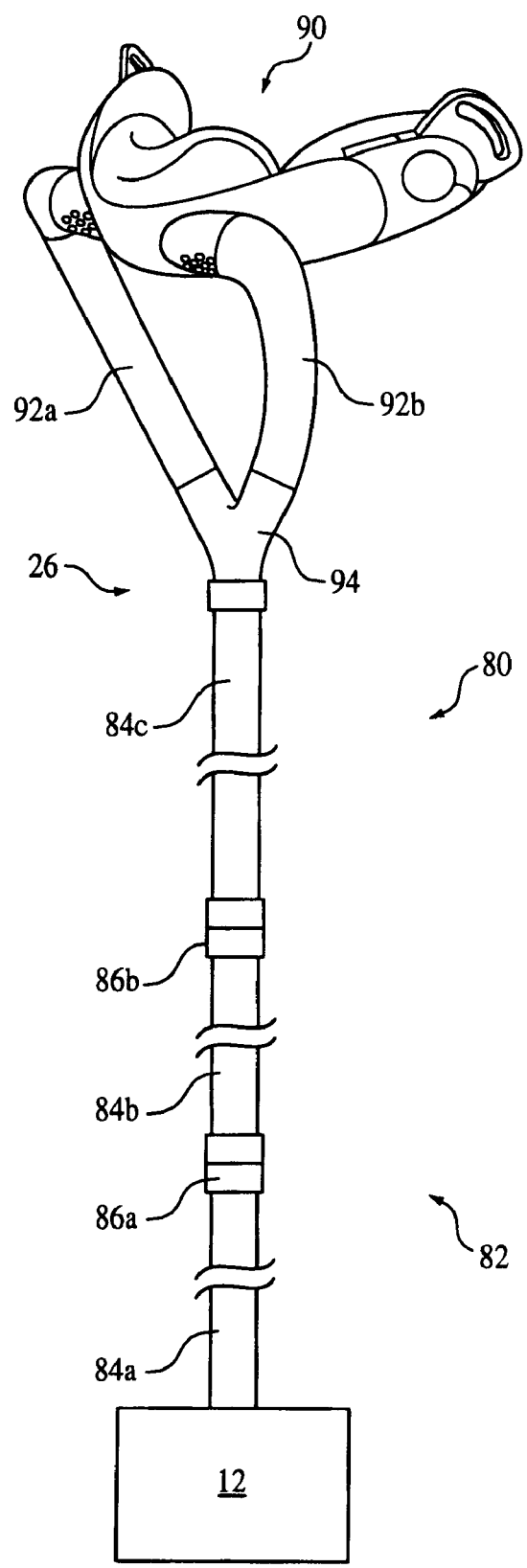
FIG. 8 is a perspective view of a pressure support system that includes a second embodiment of a conduit assembly according to the principles of the present invention.
Figure 9:
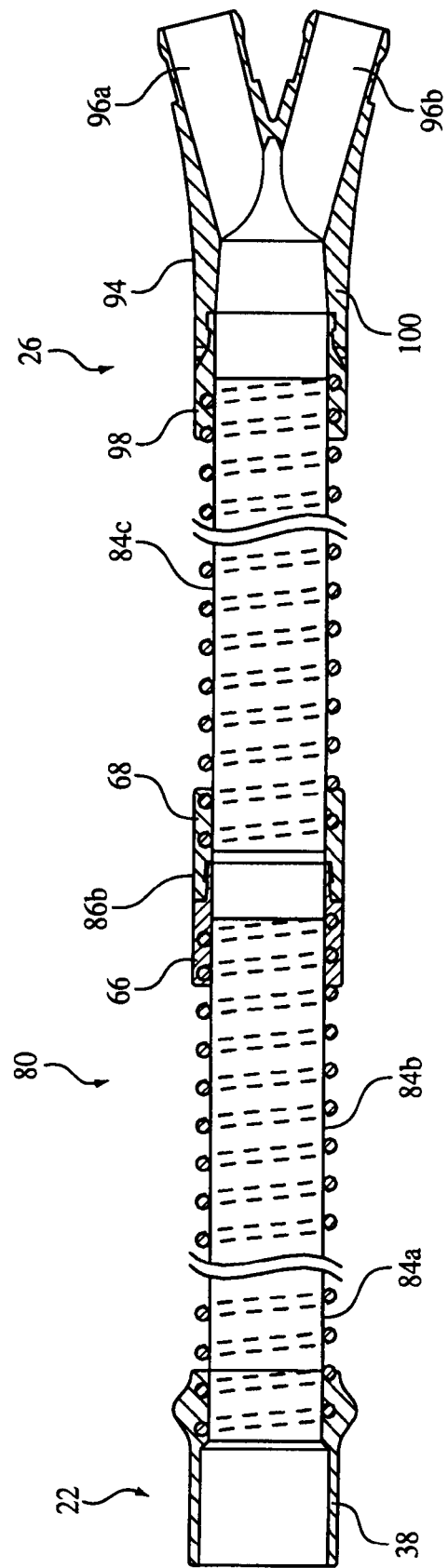
FIG. 9 is a cross-sectional view of the conduit assembly of FIG. 8.

FIGS. 8 and 9 illustrate a second embodiment of a conduit assembly 80 according to the principles of the present invention. Conduit assembly 80 is provided in a gas flow delivery system 82 that includes a gas flow/pressure generating device 12. As in the previous embodiment, conduit assembly 80 includes a plurality of flexible segments 84a, 84b, and 84c. Conduit assembly 80 also includes swivel connectors 86a and 86b that rotatably couple adjacent segments to one another. A patient interface device 90 is coupled to second end portion 26.

In the embodiment shown in FIGS. 8 and 9, patient interface device 90 includes a pair of connecting conduit 92a and 92b that couple second end portion 26 of conduit assembly 80 to the patient interface device. A splitter connector or Y-connector 94 is provided at second end portion 26 having a first leg 96a and a second leg 96b to couple to each connecting conduit 92a and 92b.

In the illustrated exemplary embodiment, Y-connector 94 includes a first portion 98 bonded to the end portion of the flexible member in the associated flexible segment and a second portion 100 rotatably coupled to first portion 98. In particular, first portion 98 is coaxial with second portion 100 and one portion can rotate around this central axis with respect to the other portion. First portion 98 of Y-connector 94 is bonded to the flexible member using any conventional technique, such as an adhesive or a weld, such as a hot weld. In addition, the present invention contemplates providing grooves in the first portion to receive the helical supports. First portion 98 is coupled to second portion 100 in any conventional manner. For example, a tongue and groove configuration can be used to couple these two elements.

Y-connector 94 or the components thereof can have any shape, size, or configuration so long as it is suitable for its intended purposes. The Y-connector and/or the components thereof can be made from any suitable material or combination of materials, including rigid, non-rigid, or semi-rigid materials. The present invention also contemplates that the Y-connector can be formed from a single component, or from multiple components, which need rotate relative to one another.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A conduit assembly adapted to deliver a flow of breathing gas to an airway of user comprising:
    a first flexible segment having a first end portion, a second end portion, and a first lumen defined therein from the first end portion to the second end portion;
    a second flexible segment having a third end portion, a fourth end portion, and a second lumen defined therein from the third end portion to the fourth end portion; and
    a first swivel connector adapted to be coupled to the second end portion of the first segment and the third end portion of the second segment such that the first segment is rotatable relative the second segment, wherein the first swivel connector includes a first portion rigidly coupled to the second end portion of the first segment and a second portion rigidly coupled to the third end portion of the second segment, wherein the first portion is rotatably coupled to the second portion, wherein the first portion includes a plurality of individual engagement structures provided along and spaced apart from one another about an outer peripheral portion of the first portion that extends circumferentially around the first portion at a first location along the first portion, the engagement structures being integrally formed with and not movable relative to the first portion, wherein the second portion includes a flat end surface extending circumferentially around the second portion, and wherein each of the engagement structures engage only the flat end surface and no other part of the second portion and create a plurality of point-contacts between the first portion and the second portion such that at any one time: (i) only a plurality of separate first radial portions spaced about the flat end surface are engaged by the engagements structures, and (ii) at each of a plurality of separate second radial portions spaced about the flat end surface no part of the second radial portion is engaged by the first portion.

2. The conduit assembly of claim 1, wherein the first end portion of the first segment is adapted to be coupled to an outlet of a pressure support device.

3. The conduit assembly of claim 1, wherein the fourth end portion of the second segment is adapted to be coupled to a patient interface.

4. The conduit assembly of claim 3, wherein the fourth end portion of the second segment is adapted to be coupled to a coupling member associated with the patient interface.

5. The conduit assembly of claim 3, wherein the fourth end portion of the second segment is rotatably coupled to the patient interface.

6. The conduit assembly of claim 1, wherein the first segment and the second segment include a flexible member and a helical support disposed around the flexible member.

7. The conduit assembly of claim 1, wherein each of the engagement structures has an arcuate-shaped end that engages the end surface to create the point contact between the engagement structure and the end surface.

8. The conduit assembly of claim 1, further comprising a heating element associated with the first segment, the second segment, or both.

9. The conduit assembly of claim 8, wherein the heating element comprises a heating wire disposed in the first lumen, the second lumen, or both.

10. A system for delivering a breathing gas to a user comprising:
   (a) a gas flow/pressure generating device adapted to produce a flow of gas, the gas flow generating device having a housing and an outlet on an exterior of the housing;
   (b) a patient interface assembly; and
   (c) a conduit assembly having a first end portion operatively coupled to the outlet of the housing and a second end portion operatively coupled to the patient interface assembly, wherein the conduit assembly carries the flow of gas from the gas flow generating device during operation of the gas flow generating system, and wherein the conduit assembly comprises:
      (1) a plurality of flexible segments; and
      (2) a swivel connector disposed between and joining adjacent segments in the plurality of flexible segments such that adjacent flexible segments are rotatable relative to one another, wherein the swivel connector includes a first portion and a second portion, wherein the first portion is rotatably coupled to the second portion, wherein the first portion includes a plurality of individual engagement structures provided along and spaced apart from one another about an outer peripheral portion of the first portion that extends circumferentially around the first portion at a first location along the first portion, the engagement structures being integrally formed with and not movable relative to the first portion, wherein the second portion includes a flat end surface extending circumferentially around the second portion, and wherein each of the engagement structures only engage the flat end surface and no other part of the second portion and create a plurality of point-contacts between the first portion and the second portion such that at any one time: (i) only a plurality of separate first radial portions spaced about the flat end surface are engaged by the engagements structures, and (ii) at each of a plurality of separate second radial portions spaced about the flat end surface no part of the second radial portion is engaged by the first portion.

11. The system of claim 10, wherein the patient interface assembly comprises:
   a shell having a first side and a second side;
   a coupling member coupled to the first side of the shell; and
   a cushion coupled to the second side of the shell, and wherein the second end portion of the conduit assembly is coupled to the coupling member.

12. The system of claim 11, wherein the coupling member is rotatably coupled to the shell, the second end portion of the conduit assembly is rotatably coupled to the coupling member, or both.

13. The system of claim 10, wherein the second end portion of the conduit assembly is rotatably coupled to the patient interface.

14. The system of claim 10, wherein each flexible segment in the plurality of flexible segments comprises a flexible member, and a helical support disposed around the flexible member.

15. The system of claim 10, wherein each of the engagement structures has an arcuate-shaped end that engages the end surface to create the point contact between the engagement structure and the end surface.

16. The system of claim 10, further comprising a heating element associated with on one or more of the plurality of flexible segments.

17. The system of claim 16, wherein the heating element comprises a heating wire disposed in one or more of the plurality of flexible segments.

18. The system of claim 10, wherein the plurality of flexible segments comprise three segments.

19. The system of claim 10, further comprising a humidifier chamber having an humidifier inlet and a humidifier outlet, wherein the humidifier inlet is operatively coupled to the outlet of the housing, and wherein the humidifier outlet is operatively coupled to the first end portion of the conduit assembly.

* * * * *